United States Patent [19]

Wheeler

[11] Patent Number: 5,133,704
[45] Date of Patent: Jul. 28, 1992

[54] INTERMITTENT BATWING ADHESIVE SYSTEM FOR SANITARY NAPKIN

[75] Inventor: Bruce Wheeler, Scotch Plains, N.J.

[73] Assignee: McNeil-PPC, Inc., New Brunswick, N.J.

[21] Appl. No.: 609,048

[22] Filed: Nov. 2, 1990

Related U.S. Application Data

[63] Continuation of Ser. No. 203,046, Jun. 6, 1988, abandoned.

[51] Int. Cl.⁵ ............................................. A61F 13/15
[52] U.S. Cl. .................................... 604/387; 604/390
[58] Field of Search ............ 604/386, 387, 390, 385.1, 604/389, 391, 392

[56] References Cited

U.S. PATENT DOCUMENTS

| | | | |
|---|---|---|---|
| 4,605,405 | 8/1986 | Lassen | 604/389 |
| 4,608,047 | 8/1986 | Mattingly | 604/387 |
| 4,615,696 | 10/1986 | Jackson et al. | 604/389 |
| 4,687,478 | 8/1987 | Van Tillburg | 604/387 |
| 4,701,178 | 10/1987 | Glaug et al. | 604/387 |
| 4,759,754 | 7/1988 | Korpman | 604/387 |
| 4,773,905 | 9/1988 | Molee et al. | 604/378 |
| 4,834,739 | 5/1989 | Linker et al. | 604/385.1 |
| 4,846,828 | 7/1989 | Mendelsohn | 604/387 |
| 4,900,320 | 2/1990 | McCoy | 604/387 |
| 4,911,701 | 3/1990 | Mavinkurve | 604/385.2 |
| 4,936,839 | 6/1990 | Molee et al. | 604/378 |

FOREIGN PATENT DOCUMENTS

| | | | |
|---|---|---|---|
| 0249924 | 12/1987 | European Pat. Off. | 604/386 |
| 0301491 | 2/1989 | European Pat. Off. | 604/386 |

*Primary Examiner*—C. Fred Rosenbaum
*Assistant Examiner*—Mark O. Polutta

[57] ABSTRACT

Winged sanitary napkins are provided which include a release strip disposed over a portion of the undergarment-facing side of the absorbent element and over an adhesive means attached to a body-facing side of at least one of the flaps. These napkins may be produced using a single adhesive applicator subsequent to folding the flaps. The release strip of this invention can be easily removed from the napkin to allow the wearer to wrap the flaps around the undergarment and secure the flaps to one another. These napkins conserve adhesive and release paper, while at same time, facilitating their use.

27 Claims, 2 Drawing Sheets

INTERMITTENT BATWING ADHESIVE SYSTEM FOR SANITARY NAPKIN

This is a continuation of application Ser. No. 203,046 filed Jun. 6, 1988, now abandoned.

FIELD OF THE INVENTION

This invention relates to protective, absorbent liners for undergarments and more particularly, to securing the side projections of winged sanitary napkins prior to use.

BACKGROUND OF THE INVENTION

Some of the more recent napkins designs, in order to address the art-recognized lateral leakage problem, have included side panels, flaps or wings that extend laterally from the longitudinal sides of a central absorbent. See U.S. Pat. Nos. 4,608,047; 4,285,343; and 4,589,876 which are hereby incorporated by reference. These products are designed to protect the undergarments of their users by wrapping around the crotch portion of an undergarment, such as a panty, in order to prevent leakage onto the undergarment.

The flaps and central absorbents of these napkins usually have body fluid impervious surfaces that face the surface of the undergarment. Usually, adhesive is disposed on their body fluid impervious surfaces as a means for attaching the product to a user's undergarment. These adhesive elements are often covered with separate release strips for packaging and shipping which act to protect the adhesive from dirt and unintended adhesion during manufacture, packaging and storage. These strips can be removed by the user immediately prior to application of the product. See U.S. Pat. Nos. 4,285,343 and 4,589,876. Multiple adhesive elements and release strips, however, can present the user with a cumbersome process when preparing the product for use. The user often has to remove three release strips located under both side panels and the central absorbent, while simultaneously attempting to prevent the flaps from inadvertently adhering to one another or to another part of the product. Should such adherence take place, the product would be rendered useless. Moreover, the additional adhesive system on the flaps can produce additional fouling of the undergarment material due to adhesive transfer. Even when the problem of undesired adhesion is avoided, the user is presented with the task of disposing of three release strips.

One proposed solution to some of these problems has been to provide packaged winged napkins with adhesive located on an undergarment-facing side of their central absorbent element and on an undergarment-facing side of one or both of folded flaps, with a protective release strip located between the adhesive on the flaps and that of the central absorbent. See U.S. Pat. No. 4,701,178, which is herein incorporated by reference. While such products conserve release strip material and avoid inadvertent adhesion of the flap adhesive, they generally require that the release strip be treated so that both sides of the strip have releasable coatings on them.

Furthermore, napkins that provide release paper between their flaps and central absorbent can be damaged during preparation for use. A user may deform the product when removing the release strip, as the release strip would tend to pull at the junction between the flaps and the central absorbent. The potential for damaging the napkin is even greater when the flaps overlap and one flap bears adhesive. In such designs, the release strip would exert a tensile force upon the flaps prior to releasing the adhesive between them. This force could damage one or both flaps due to stretching or tearing, prior to the disengagement of the flap-to-flap adhesive element.

Accordingly, a need exists for a sanitary napkin having side protecting flaps and can be manufactured using a single release paper strip. There is also a need for a winged sanitary napkin which can applied without transferring adhesive to a user's undergarment.

It is therefore an object of this invention to provide a winged sanitary napkin that can be manufactured with a single release paper strip.

It is another object of this invention to provide a winged sanitary napkin that is garment-protecting, and can be prepared for application without a risk of damaging its flaps.

With these and other objects in view which will become apparent hereinafter, this invention resides in the novel construction, combination, arrangement of parts and methods substantially as hereinafter described and more particularly defined in the attached claims.

SUMMARY OF THE INVENTION

A winged sanitary napkin is provided having a body facing side and a garment facing side and, further, having a release strip disposed over a portion of the undergarment-facing side of the absorbent element and over an adhesive means attached to the body-facing side of at least one of the flaps. A napkin according to this invention may be produced by folding the flaps toward the garment-facing side of the napkin and applying adhesive subsequent to folding the flaps using a single adhesive applicator. A release strip can be applied over the adhesive on the flaps, and can be easily removed without stretching or otherwise damaging the flaps. Unlike some prior art napkins which employ a single release strip coated on both sides with a releasable coating, such as silicone, the preferred release strip of this invention need only be coated on one side, as only one side is in contact with adhesive. Moreover, because the adhesive disposed on the flap is designed to adhere to the other flap of the napkin during use, less adhesive is in contact with the undergarment and less adhesive transfer can occur than in prior art napkins.

Accordingly, sanitary napkins are provided which provide adhesive bonding between the flaps during the securement of the napkin to the undergarment. These napkins are, moreover, easy to apply because the release strips can be removed in a single motion with minimal risk of damaging the flaps.

In the more preferred embodiments of this invention, the release strip can be applied to the adhesive of the central absorbent and the adhesive on a body-facing side of one or more of the flaps, such that a user may expose both adhesives with one continuous stripping motion. The adhesive on the central absorbent can be intermittent, i.e., disposed substantially only near the transverse ends of the absorbent element, such that the flaps are not adhered to the undergarment-facing side of the central absorbent prior to use. Additionally, the adhesive on the flap and central absorbent can be disposed approximately collinearly, so that a standard-sized release paper can be employed.

BRIEF DESCRIPTION OF THE DRAWINGS

The accompanying drawings illustrate a complete embodiment of the invention according to the best mode for the best practical application of the principles thereof and in which.

DESCRIPTION OF THE INVENTION

Figure 1:
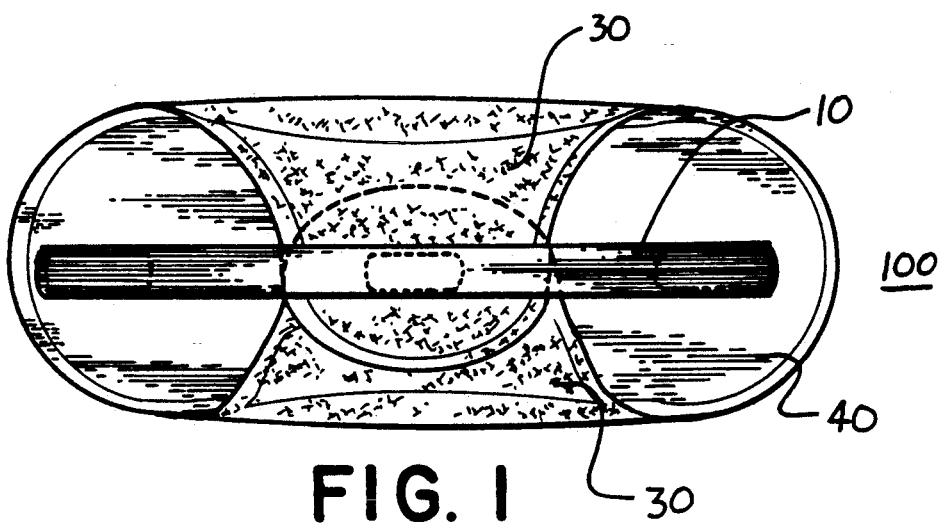
FIG. 1 is a planar view of the "as-packaged", undergarment-facing side of a sanitary napkin embodiment of this invention illustrating a single release paper disposed over the adhesive means of the central absorbent and one of the flaps.
Figure 2:
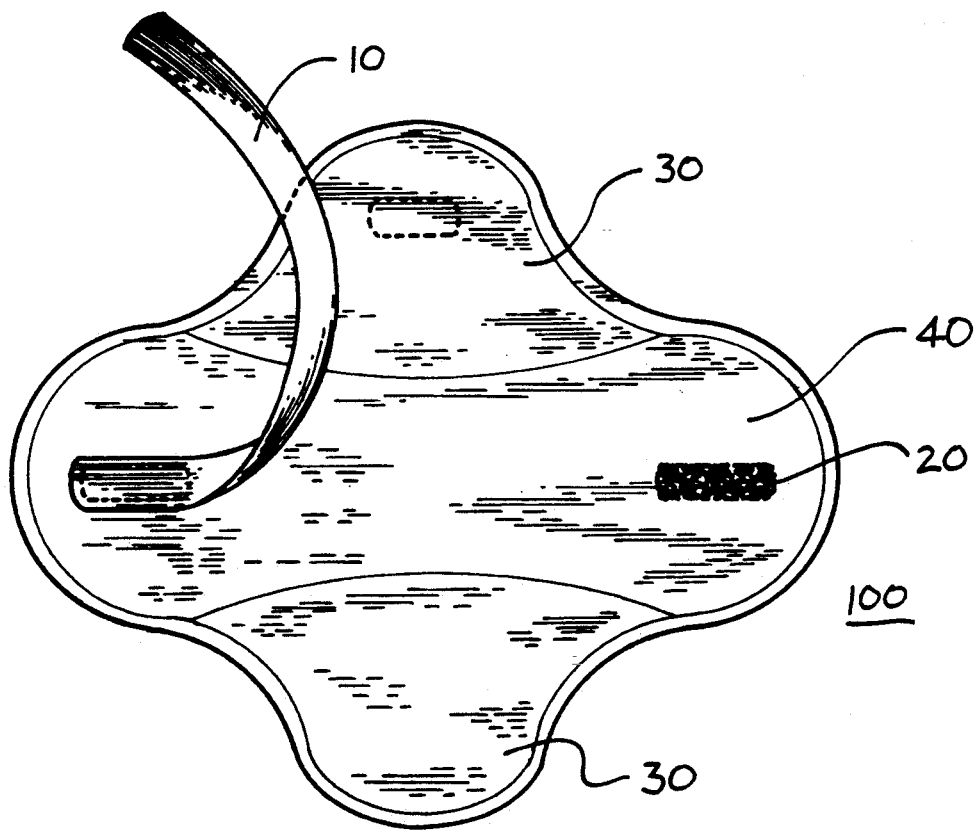
FIG. 2 is a planar view of the undergarment-facing side of the sanitary napkin embodiment of FIG. 1, wherein the release strip is partially removed for permitting the flaps to open prior to application of the napkin to an undergarment.
Figure 3:
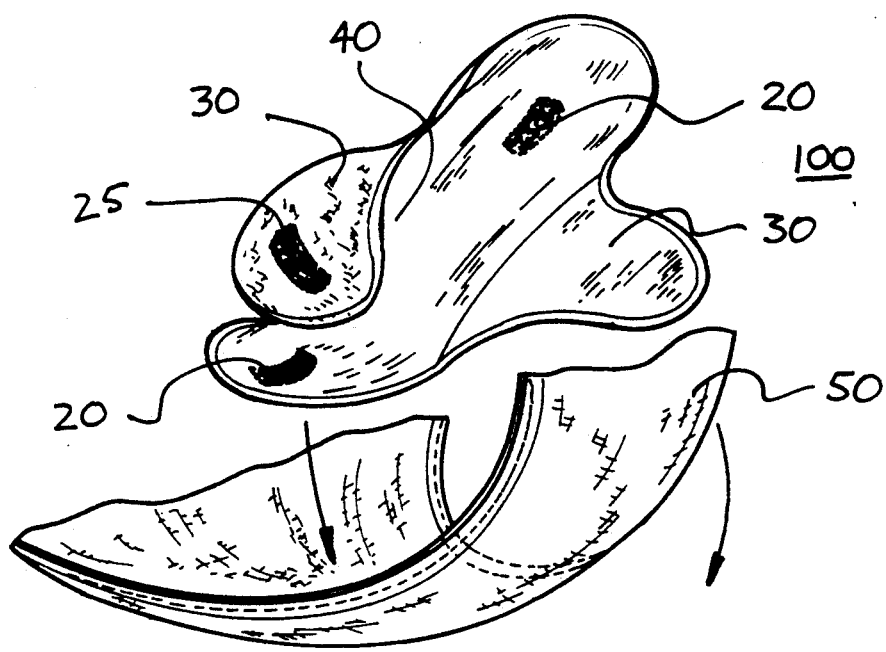
FIG. 3 is a perspective view of an application of the sanitary napkin of FIG. 1 prior to securing to an undergarment.
Figure 4:
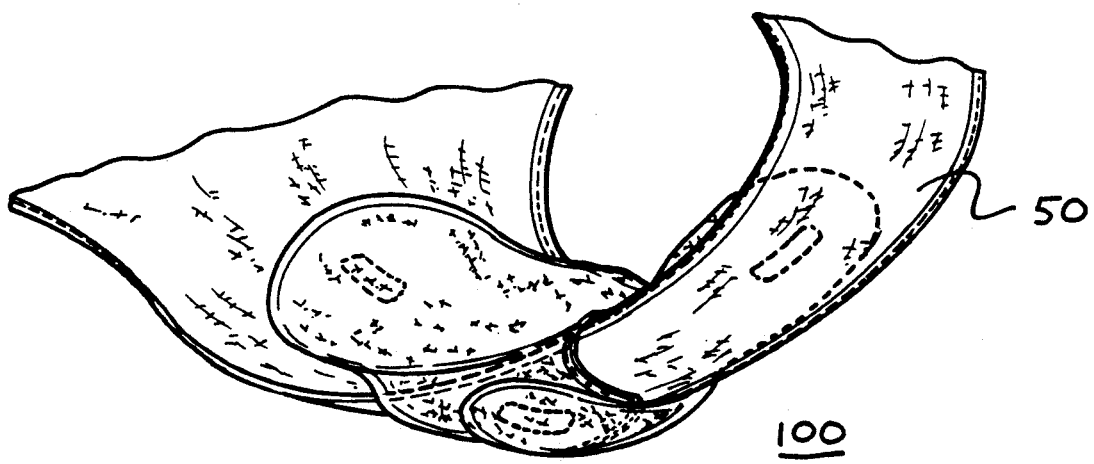
FIG. 4 is a perspective view of the final application of the sanitary napkin FIG. 1, whereby the napkin is disposed onto a crotch portion of an undergarment and the flaps are secured to one another with adhesive.

FIGS. 1 and 2 depict a preferred sanitary napkin 100 having an absorbent element 40 with longitudinally extending sides, transverse ends, a body-facing side and an undergarment- facing side. The napkin includes at least one flap extending laterally from one of the longitudinal sides of the absorbent element 40. The flap comprises adhesive means disposed on its body-facing side. The napkin 100 also includes a release strip 10 having a releasable surface overlapping a portion of the undergarment-facing side of the absorbent element 40, whereby the flap is folded over the undergarment- facing side of the absorbent element 40 and disposed to adhere its adhesive means with the releasable surface of the release strip 10.

Preferably, napkin 100 has a single release strip 10, which is preferably releasably attached to the adhesive system for both central absorbent element 40 and flaps 30. Release strip 10 is preferably manufactured using kraft paper, as is customary in the art. It can be of standard dimensions, and can be coated with a releasable coating, i.e. silicone, on its adhesive-contacting side.

Also included with this invention are attachment adhesives elements 20 and 25 which can be made of any known, pressure-sensitive adhesive material. As used herein, the term "pressure-sensitive" refers to any releasable adhesive or releasable tenacious means. Adhesive compositions suitable for sanitary napkins, include, for example, the water-based, pressure-sensitive adhesives such as acrylate adhesives. Alternatively, the adhesive may comprise rapid setting thermoplastic "hot-melt", rubber adhesives, or two-sided adhesive tape. Adhesive elements 20 and 25 can be roughly symmetrically sized, i.e., at least having approximately equal transverse widths, or alternatively, having two or more smaller adhesive portions. They can be disposed approximately "collinearly"; i.e., a single, preferably rectangular, release strip 10 of less than about 3 inches in width could be employed to cover them. Adhesive elements 20, preferably are located substantially near the transverse ends of the absorbent element 40, within about 0.1 to 3.0 inches from the transverse ends of the napkin 100. Alternatively, a "full-length" adhesive system, such as those currently available in the art, could be applied to the absorbent element 40 in combination with the preferred adhesive system applied to the single flap. The adhesive means for the flap may be disposed on both flaps 30, although this is not preferred.

Thus, in accordance with this invention, one adhesive element 25 can be used for securing the flaps 30 together around the undergarment 50, without any tabs or other adhesive means on the flaps and, therefore less adhesive can be used than in prior art constructions. Furthermore, because the flaps are attached to one another during use, they do not cause adhesive fouling on the exterior of the crotch portion of undergarment 50.

Adhesive elements 20 and 25, can be provided on the napkin using any of the art-recognized manufacturing methods. These may include providing a continuous line of adhesive across a folded napkin so as to provide adhesive on the undergarment-facing side of absorbent element 40 and on one of flaps 30. Alternatively, adhesive could be applied using a spot adhesive applicator, so as to provide adhesive portions on absorbent element 40 and at least one of flaps 30. Adhesive may also be applied to release paper strip 10, and then transferred via the application of strip 10 to the undergarment-facing side of the central absorbent and to the body-facing side of flap or flaps 30.

A napkin of this invention can be applied by folding flaps 10 over a crotch portion of an undergarment 50 and by adhering adhesive elements 20 to the crotch area of undergarment 50. Flaps 30 are laterally extended from their folded, pre-use position and allowed to fold over an outside portion of the crotch area. Flaps 30 are then preferably attached to one another with adhesive element 25, which is preferably disposed on the body-facing side of one of the flaps 30.

Absorbent element 40 can contain conventional resilient material for enabling napkin 100, to bend easily without excessive distortion. Preferably, absorbent element 40 is approximately 4–12 inches long, more preferably about 8–11 inches. Absorbent element 40 preferably has a core, which may be made of loosely associated absorbent hydrophilic materials such as cellulose fibers, wood pulp, regenerated cellulose or cotton fibers, a combination of cellulose fibers and hydrocolloidal material as described in U.S. Pat. No. 4,551,142 (Kopolow), synthetic hydrophilic fibers, and/or like materials generally known in the art to be useful as absorbent materials. The absorbent element 40 may be rectangular or shaped.

As is customary in the art, the body-facing side of the napkins 100 should be covered with a body-fluid pervious surface. A body-fluid pervious surface can be made of a flexible, relatively non-absorbing fluid pervious material. This material is provided for comfort and conformability and directs fluid to an underlying layer, for example wood pulp, which retains such fluid. These surfaces may be woven, or non-woven fabric pervious to body fluid. Furthermore, they should retain little or no fluid in their structure so as to provide a relatively dry surface next to the skin. Generally, the fluid permeable surface is a single sheet of material having a width sufficient to cover the body-facing side of the absorbent elements. Preferably, the fluid pervious surface is longer than the core so it can be formed into end tabs, and mechanically or chemically sealed together with other pervious or non-pervious layers to fully enclose the absorbent core. The fluid pervious surface is preferably made of fibers or filaments of thermoplastic polymers such as lower polyalkylenes (e.g. polyethylene or polypropylene) or apertured polymeric film such as that set forth in U.S. Pat. No. 4,690,679.

Underlying the core of the absorbent element can be another layer of absorbent material to provide additional resiliency to the product. This layer can extend beyond the longitudinal sides of the absorbent core to entrap any body fluid which escapes from the sides of the absorbent element 40. This layer may also be substantially wider than the core of the absorbent element 40 and may extend into the flaps 30. The absorbent layer may comprise a thin, absorbent layer of material such as tissue, fabric, or the like, made of cellulosic fibers. Because such material is provided as a safety measure and is only required to contain escaped fluid, it need not be very absorbent at all, and, in fact, may be comprised of any capillary or cellular system including hydrophobic material. However, the preferred material is a hydrophilic fabric made up of cellulosic fibers such as wood pulp tissue or other suitable hydrophilic woven or nonwoven material. The preferred tissue has the advantage of providing resiliency and conformability to the product.

A sanitary napkin made in accordance with this invention further can include a body-fluid impervious surface on its undergarment-facing side. The impervious surface preferably allows air and moisture vapor to pass through it while blocking the passage of fluid to the outer surface. The impervious surface may be heat sealed or fastened by way of adhesives to the absorbent core or to an absorbent core wrapped in a pervious surface cover. The impervious surface may be made from any thin, flexible, body fluid impermeable material such as, for example, a polymeric film, e.g. polyethylene, polypropylene, cellophane or a normally fluid pervious material treated to be impervious, such as impregnated fluid repellent paper or coated non-woven fabric material. In the most preferred embodiments of this invention, the impervious surfaces include a plastic film of polyethylene or a bicomponent film such as an ethylene vinyl acetate/polyethylene (EVA/PE) coextruded film.

The flaps of the sanitary napkins of this invention are preferably made of a stretchable, flexible material. The flaps can include a body fluid impervious backing such as the materials described above. Preferably, they do not contain bulky, low density absorbent materials. The flaps can have body fluid pervious covers and absorbent tissues disposed between their covers and fluid impervious backings. The flaps should contain absorbent tissue with sufficient capillary action to retain small quantities of escaped liquid. This tissue can be heat sealed or adhesively sealed around the edges of the flaps with the preferred impervious backings and body fluid pervious covers of the flaps to form absorbent areas.

From the foregoing it can be realized that this invention provides sanitary napkins which conserve adhesive and release paper, while at the same time facilitating their use. The napkins are garment-protecting, since they do not require that their flap adhesive systems be secured to the undergarment. Various embodiments have been illustrated solely for the purpose of describing, but not for the purpose of limiting, the scope of the invention. Various modifications, which will become apparent to one skilled in the art, are within the scope of this invention described in the attached claims.

What is claimed is:

1. A sanitary napkin comprising:
   (a) an absorbent element having longitudinally extending sides, transverse ends, a body-facing side and a garment-facing side;
   (b) at least one flap extending laterally from one of said longitudinal sides of said absorbent element, said flap having a body-facing side and a garment-facing side, said body-facing side being contiguous with the body-facing side of said absorbent element and said garment-facing side being contiguous with the garment-facing side of said absorbent element, said flap containing adhesive means disposed on the body-facing side of said flap;
   (c) at least one area of said garment-facing side of said absorbent element containing adhesive means disposed such that said adhesive means is longitudinally aligned collinearly with the adhesive means disposed on the body-facing side of said flap when said flap is folded transversely across the garment-facing side of said absorbent element; and
   (d) a release strip having a releasable surface which is releasably attached to the adhesive means disposed on said flap and capable of being attached simultaneously to the adhesive means disposed on the garment-facing side of the absorbent element.

2. A sanitary napkin according to claim 1 wherein said adhesive-containing flap is folded such that its garment-facing side is in partial contact with the garment-facing side of the absorbent element.

3. A sanitary napkin according to claim 1 wherein said napkin comprises at least two flaps extending laterally from each of said longitudinal sides of said absorbent element.

4. A sanitary napkin according to claim 3 wherein each of said flaps contains adhesive means.

5. A sanitary napkin according to claim 3 wherein the garment-facing side of each of said flaps is in at least partial contact with the garment-facing side of said absorbent element.

6. A sanitary napkin according to claim 1 wherein said absorbent element contains adhesive means on the garment-facing side.

7. A sanitary napkin according to claim 6 wherein said adhesive means comprises at least two adhesive elements disposed on said garment-facing side of the absorbent element substantially near said transverse ends of said absorbent element.

8. A sanitary napkin according to claim 7 wherein said release strip is disposed over said adhesive means of said flap and said two adhesive elements of said absorbent element.

9. A sanitary napkin according to claim 8 wherein said adhesive means of said flap and said two adhesive elements have collinear portions.

10. A sanitary napkin according to claim 9 wherein said adhesive means of said flap and said two adhesive elements of said absorbent element have approximately equal transverse widths.

11. A sanitary napkin comprising:
    (a) an absorbent element having longitudinally extending sides, transverse ends, a body-facing side and a garment-facing side, said absorbent element having adhesive means disposed on its garment-facing side;
    (b) a pair of flaps extending laterally from each of said longitudinal sides of said absorbent element, at least one of said flaps containing adhesive means disposed on a body-facing side of said flap, said body-facing side of said flap being contiguous with said body-facing side of said absorbent element, said flaps being folded over onto said garment-facing side of said absorbent element; and (c) a single release strip having a releasable surface disposed to adhere to said adhesive means of said flap and to the adhesive means of said absorbent element.

12. A method of applying a release strip to a sanitary napkin comprising:
(a) providing a sanitary napkin having an absorbent element having longitudinally extending sides, transverse ends, a body-facing side and a garment-facing side,
(b) disposing adhesive means on said garment-facing side of said absorbent element,
(c) said napkin further including at least one flap extending laterally from one of said longitudinal sides of said absorbent element, said flap having a body-facing side contiguous with the body-facing side of said absorbent element and said flap further having a garment-facing side contiguous with the garment-facing side of said absorbent element, said method further comprising folding said flap across the garment-facing side of said absorbent element and thereafter disposing adhesive means on a body-facing side of said flap such that the adhesive means disposed on the garment-facing side of said absorbent element and the adhesive means disposed on the body-facing side of said flap are collinear along a longitudinal axis of said sanitary napkin;
(d) folding said flap over said undergarment-facing side of said absorbent element, whereby said adhesive means is exposed; and
(e) disposing a release strip having a releasable surface thereon over a portion of said undergarment-facing side of said absorbent element so that said releasable surface is adhered with said adhesive means disposed on said body-facing side of said flap and capable of being adhered with said adhesive means disposed on said garment-facing side of the absorbent means.

13. A method according to claim 12 wherein said providing step provides a sanitary napkin having at least two flaps extending laterally from each of said longitudinal sides of said absorbent element.

14. A method according to claim 13 wherein said folding step comprises folding each of said flaps over said garment-facing side of said absorbent element, whereby said adhesive means is exposed.

15. A method according to claim 14 wherein a sanitary napkin is provided having adhesive means on the garment-facing side of said absorbent element.

16. A method according to claim 15 wherein said disposing step comprises disposing said release strip in contact with said adhesive means on both said flap and said absorbent element.

17. A method according to claim 16 wherein said providing step further comprises providing a sanitary napkin having at least two adhesive elements disposed on said undergarment-facing side of said absorbent element substantially only near said transverse ends of said absorbent element.

18. A sanitary napkin made by the method of claim 12.

19. A sanitary napkin made in accordance with the method of claim 12 wherein said adhesive-containing flap is folded such that its garment-facing side is in partial contact with the garment-facing side of the absorbent element.

20. A sanitary napkin made in accordance with the method of claim 12 wherein said napkin comprises at least two flaps extending laterally from each of said longitudinal sides of said absorbent element.

21. A sanitary napkin according to claim 20 wherein each of said flaps contains adhesive means.

22. A sanitary napkin according to claim 20 wherein the garment-facing side of each of said flaps is in at least partial contact with the garment-facing side of said absorbent element.

23. A sanitary napkin made in accordance with the method of claim 12 wherein said absorbent element contains adhesive means on the garment-facing side.

24. A sanitary napkin according to claim 23 wherein said adhesive means comprises at least two adhesive elements disposed on said garment-facing side of the absorbent element substantially near said transverse ends of said absorbent element.

25. A sanitary napkin according to claim 24 wherein said release strip is disposed over said adhesive means of said flap and said two adhesive elements of said absorbent element.

26. A sanitary napkin according to claim 25 wherein said adhesive means of said flap and said adhesive elements have collinear portions.

27. A sanitary napkin according to claim 26 wherein said adhesive means of said flap and said two adhesive elements of said absorbent element have approximately equal transverse widths.

* * * * *